United States Patent [19]

Falk

[11] 4,389,316

[45] Jun. 21, 1983

[54] METHOD AND A DEVICE FOR LIQUID CHROMATOGRAPHY

[75] Inventor: Bengt G. Falk, Upsala, Sweden

[73] Assignee: Pharmacia Fine Chemicals AB, Upsala, Sweden

[21] Appl. No.: 263,128

[22] Filed: May 13, 1981

[30] Foreign Application Priority Data

May 14, 1980 [SE] Sweden .................................. 8003645

[51] Int. Cl.³ ............................................. B01D 15/08
[52] U.S. Cl. .................................... 210/656; 210/101; 210/198.2
[58] Field of Search ..................... 210/101, 198.2, 635, 210/656

[56] References Cited

U.S. PATENT DOCUMENTS 3,934,456  1/1976  Munk ............................... 210/198.2
3,954,617  5/1976  Ishimatsu ......................... 210/198.2

OTHER PUBLICATIONS

High Performance Liquid Chromatography by Knox Edinburg University Press, 1978.

*Primary Examiner*—John Adee
*Attorney, Agent, or Firm*—Fred Philpitt

[57] ABSTRACT

A method and a device for applying a sample solution to a liquid chromatographic column. The device comprises a container of uniform cross section and a piston slidably arranged in said container and sealingly contacting the container wall so as to divide the container into a driving solution chamber and a sample solution chamber. The piston is arranged to be displaced towards the sample solution chamber when driving solution is pumped into the driving solution chamber while expelling sample solution from the sample solution chamber in an amount proportional to the amount of driving solution pumped into the driving solution chamber. When all sample solution has been expelled from the sample solution chamber the driving solution chamber is automatically put into communication with the outlet of the container.

8 Claims, 3 Drawing Figures

METHOD AND A DEVICE FOR LIQUID CHROMATOGRAPHY

The present invention relates to a new method and a new device for applying a desired amount of a liquid sample on a chromatographic column or the like.

Liquid chromatography is a well known separation technique which is utilized for separating various components contained in a sample. In this technique the sample is applied to a column of a chromatography material, e.g. gel particles, and a a suitable solvent (eluent) is then allowed to pass through the column, bringing with it at least certain of the components contained in the sample. The various components of the sample will then, depending on different co-operation with the chromatography material, pass through the column at different speeds, thereby making it possible to efficiently separate the various components of the sample from each other.

A prerequisite for obtaining optimal results in liquid chromatographic separation is that the sample has to be applied on the column correctly. A common method of applying the sample on the column is to apply the desired amount by means of an injection syringe. This manual method has obvious limitations which i.a. make automatization impossible. Attempts have been made to automate the technique by means of a valve device, which makes it possible to supply eluent to the column in two different ways. In a first position the eluent passes via the valve directly to the column, and in this position a desired amount of the sample can be injected into a supply loop connected to the valve. When the desired amount of the sample has been loaded in the supply loop the valve is switched so that the eluent now is fed to the column via the supply loop, the eluent then pressing out the sample on the column. After the application of the sample the valve can be reset to the original position, a new sample can be charged in the supply loop, and so on.

It is true that this technique permits automation of the process, but a essential drawback is that the capacity of the sample loop has to be chosen for the greatest amount of sample to be loaded, for example 50 ml for preparative purposes. This means that the hose shaped sample loop has to be made very long, which in turn results in relatively great dilution of the sample when smaller samples (e.g. down to 5 $\mu$g for analytic purposes) are to be loaded. This affects the result detrimentally. As an alternative one can switch between supply loops of the different sizes, which leads to obvious practical drawbacks.

The present invention aims at solving these and other problems in the application of a sample solution on liquid chromatographic columns, and it in particular aims at providing an application method and an application device permitting automated application of small as well as large samples without undue dilution thereof and without having to interrupt the flow to the column for the application of the sample. The invention also makes it possible to dose sample solution repeatedly without having to load a new sample each time, and this irrespective of the desired sample volume.

These and other advantages are obtained in accordance with the invention by means of the method and the device for sample application defined in the following claims and described in more detail below.

One basic idea of the invention is thus to make use of a sample container, which by means of a freely mounted piston is divided into a driving solution chamber and a sample chamber. The piston is slidable in the tubular container while sealing against the container wall so that the two chambers normally do not communicate with each other. The driving solution chamber can be connected to a source of driving solution, in particular an eluent, whereas the sample chamber can be connected to the column. When driving solution is pumped into the driving solution chamber the piston, which serves as a partition, will be forced against the sample chamber and press out sample solution to the column in an amount directly proportional to the amount of pumped driving solution. Since the driving solution chamber is not in communication with the sample chamber, the driving solution will not be mixed with the sample, no dilution thereof thus taking place, and this irrespective of how great or small an amount of sample is pumped out.

The device according to the invention can be connected to the drive solution source and the column respectively by means of an adjustable valve of conventional type, the driving solution being pumped into the driving solution chamber for the time during which the sample is to be loaded. After the desired amount of sample has been discharged the valve is switched such that the driving solution will be pumped directly to the column. Because the amount of sample pressed out from the sample chamber is directly proportional to the amount of driving solution pumped into the driving chamber the sample voume can be controlled and varied in simple manner. For example, a constant pumping seed pump can be used, in which case the amount of sample loaded will be directly proportional to the time during which the valve is open to the application device. The sample volume can then be adjusted by means of a simple time based control unit, which controls the time during which the valve is open towards the application device.

It is preferred to provide the container with a cooling jacket to keep the sample at a suitable temperature. In this way one can, for example, already in the morning charge a comparatively great amount of sample solution in the container and then during the day apply several smaller samples on the column at desired times and in desired amounts.

In an alternative embodiment the sample volume can be determined by only filling the sample chamber with a desired one-shot dose of the sample solution. The container is designed such that the driving solution chamber is put into communication with the outlet from the sample chamber when the separating piston has reached its bottom position in the chamber chamber, i.e. when all sample solution has been discharged from the sample chamber. This can, for example, by achieved by providing one or several slots in the container wall at the bottom portion of the sample chamber, so that the drive solution can flow through these slots around the piston when the same has reached its bottom position. This arrangement makes it possible to discharge the sample from the sample chamber without being mixed with the driving solution as long as there is still sample left in the sample chamber, while at the same time ensuring a continuous flow from the container in that the driving solution can flow out immediately following the sample solution. The connection of the driving solution chamber to the outlet of the container when all sample solution has been discharged also serves as a safety valve, i.e. prevents harmful overpressures from occurring in the driving solution chamber.

The expression "sample solution" is here to be understood in its broadest sense, viz. as an arbitrary solution (or possibly suspension) which is to be applied to a column in determined exact amounts. Apart from sample solutions containing several components to be separated, the same can also consist only of solvent or eluent, which are to be applied to the column in given amounts or proportions intermittently in a gradient mixing operation. In this case the driving solution can, for example, consist of the second solvent or eluent for the gradient mixing, the driving solution being alternatingly pumped directly to the column and to the driving solution chamber respectively for pumping out the first eluent from the sample solution chamber to the column.

These and other characteristics and advantages of the method and the device according to the invention will be explained in more detail in connection with a special embodiment, to which the invention however is not limited, reference being made to the enclosed drawings, wherein.

Figure 1:
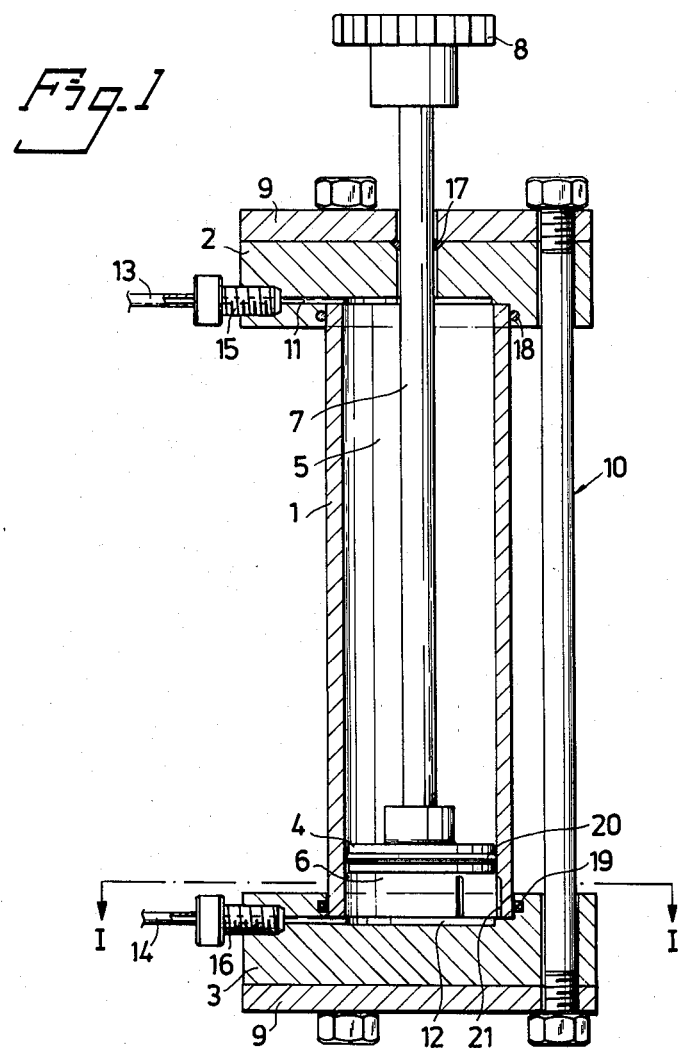
FIG. 1 is a schematic view in longitudinal section of one embodiment of the sample container according to the invention.
Figure 2:
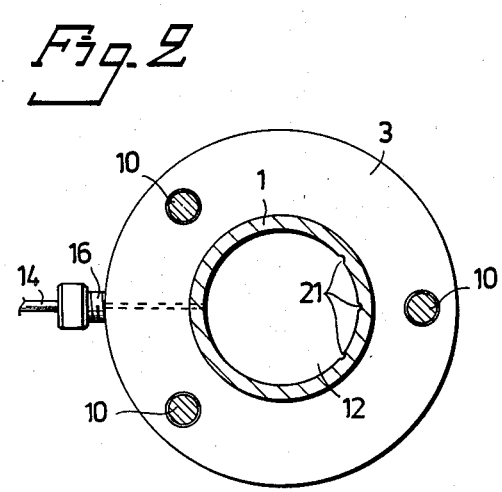
FIG. 2 shows the bottom portion of the sample container viewed according to the arrows I—I of FIG. 1.

The sample container shown in FIGS. 1 and 2 essentially consists of a container tube 1, which is provided with an upper sealing cap 2, a lower sealing cap 3 and a piston 4 slidably mounted in the tube 1. The piston 4 divides the space inside the tube 1 into an upper chamber 5, herein called driving solution chamber, and a lower chamber 6, herein called sample solution chamber. In the embodiment shown the piston 4 is connected to a piston rod 7 extending through the upper sealing cap 2 and externally thereof being provided with a control handle 8. The unit formed by the tube 1 and the sealing caps 2, 3 is kept together by means of attachment plates 9 and bolt joints 10.

The upper sealing cap 2 is provided with an inlet channel 11 for supplying driving solution to the driving solution chamber 7, whereas the lower sealing cap 3 in corresponding manner is provided with an outlet channel 12 for sample solution (when required also for driving soluton, as will be explained further below). The feed channel 11 can in any suitable manner be connected to a supply conduit 13 for driving solution, whereas the outlet channel 12 in corresponding manner can be connected to any suitable outlet conduit 14. In the case specifically shown the conduits 13 and 14 are connected to the corresponding channels 11 and 12 by means of connection sleeves 15 and 16 respectively, which are screwed into the corresponding sealing caps 2 and 3. Sealings 17 seal between the piston rod 7 and the upper sealing cap 2, sealings 18 between the tube 1 and the sealing cap 2, and sealings 19 between the tube 1 and the lower sealing cap 3. The piston 4 is on its circumference provided with a sealing ring 20, which secures sealing against the inner wall of the tube 1 while at the same time permitting sliding displacement of the piston 4 inside the tube 1.

The tube 1 is at its bottom portion provided with slots 21 in its inner surface. The slots 21, which preferably are located opposite the outlet 14 in order to secure washing away of the last remainder of sample solution from the outlet channel or space 12, have a height such that they put the driving solution chamber 5 into communication with the outlet 12 just when all sample solution has been discharged from the sample solution chamber 6 (the volume of which then will become essentially zero).

Figure 3:
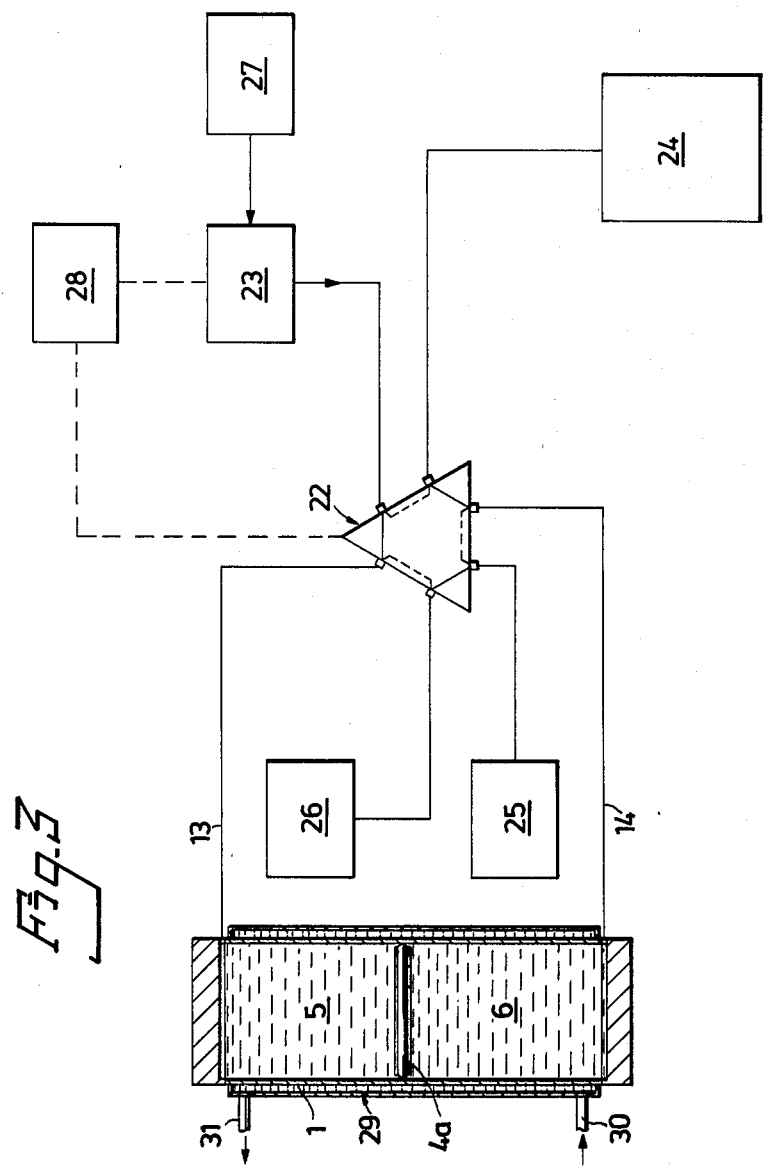
FIG. 3 is a schematic diagram illustrating one embodiment of the sample application method according to the invention.

The described sample container in principle functions in the following way. The piston 4 is moved to its bottom position by means of the control handle 8. If the tube 1 is not cleaned the conduit 14 can at first be connected to washing/rinsing solution, which is pumped into and out of the chambers 5, 6 several of times by moving the piston alternatingly upwards and downwards. The piston is then again moved to its bottom position and the conduit 14 is connected to the desired sample solution, which is sucked into the sample solution chamber 6 by moving the piston 4 upwards. Either an indetermined or roughly estimated amount of sample solution or, for a one-shot dose, exactly the desired amount of sample solution can be charged. To this end the tube 1 may be graded in any suitable scale. When charging a greater amount of sample solution to be portioned out for an extended period of time it is suitable to provide the tube 1 with a cooling jacket, possibly thermostat controlled, since sample solutions of the intended type often are temperature sensitive. FIG. 3 schematically shows a water cooling jacket 29 of conventional type, having a lower cooling water inlet 30 and an upper outlet 31. When the desired volume of sample solution has been charged in the tube 1 (it also being secured that the driving solution chamber 5 has been filled with driving solution) the sample solution is portioned out through the conduit 14 when driving solution is pumped into the conduit 13, as will be described in more detail below with reference to FIG. 3. When all sample solution has been expelled (intentionally or unintentionally) continuity in the outflow through the conduit 14 is secured since the drive solution then will be put into communication with the outlet 12 thanks to the slots 21 provided in the tube wall.

FIG. 3 schematically shows a sample container connected to an adjustable valve 22 of a type known as such. The sample container has the same basic structure as in to FIGS. 1 and 2, i.e. it essentially comprises a container tube 1 and a piston 4a, which is slidably mounted in the tube 1 and which sealingly defines a driving solution chamber 5 and a sample solution chamber 6. Although it is preferred to make use of a sample container of the type shown in FIG. 1, i.e. which makes it possible to manually control the piston 4 from the exterior by means of the piston rod 7 and the control handle 8, the invention also comprises use of a free piston 4a according to FIG. 3.

The valve 22 shown in FIG. 3 is connected to the conduits 13 and 14 and further to a pump 23 and a column 24, to which a sample is to be applied. The valve 22 is further connected to a sample solution supply 25 and a driving solution supply 26. The driving solution delivered by the pump 23 is taken from the second driving solution supply 27 (which may the same as the driving solution supply 26). The pump 23 preferably is of the constant flow type. The valve 22 is connected to any suitable time based control unit 28.

The valve 22 is adjustable between a sample application position and an elution position. The unbroken connection lines in the valve 22 mark the sample application position, whereas the broken connection lines mark the elution position. In the sample application position, shown in full lines, the pump 23 pumps driving solution 27 through the conduit 13 to the driving solution chamber 5, the outlet conduit 14 communicating with the column 24. The remaining connections in the valve are basically unessential. In the elution position, shown in broken lines, the pump 23 feeds sample solution 27 directly to the column 24, the feed conduit 13 being connected to the driving solution source 26 and the outlet conduit 14 being connected to the sample solution source 25. In analogy with what has been described in connection with FIG. 1 it is then possible to wash the container 1 and refill sample solution by alternatingly pumping driving solution through the conduit 13 and sample solution through the conduit 14. Of course, the same result can be obtained without going via the valve 22.

The system illustrated in FIG. 3 can according to the invention be used in the following way. The desired amount of sample solution is sucked into the sample solution chamber 6 as described above, the driving solution chamber 5 being kept filled with driving solution. When the sample solution is to be applied to the column 24 the valve is set to the sample application position, shown in full lines, so that the pump 23 pumps driving solution into the driving solution chamber 5 via the conduit 13. The piston 4a will thereby be forced downwards while expelling sample solution through the conduit 14 and further to the column 24. When the desired amount of sample solution has been loaded on the column 24 the driving solution supply to the chamber 5 is interupted, which in the shown embodiment takes place by resetting the valve 22 to the elution position marked by broken lines. On this resetting the flow from the pump 23 will be fed directly to the column 24. The sample container 1 is then disconnected and it can, when needed, be filled with new sample solution from the supply 25, be rinsed and charged with another sample solution, etc.

The adjustment of the valve 22 can be made manually, but it is preferably performed by the control unit 28, which automatically resets the valve when the desired amount of sample has been discharged. When using a pump 23 of the constant flow type the control unit 28 is suitably time based since the amount of discharged sample solution then will be directly proportional to the time during which driving solution is pumped into the chamber 5 by the pump. The control unit 28 can thus be a simple timer mechanism of conventional type, which resets the valve 22 after a desired set time. For practical reasons the control unit 28 is preferably graded in volume instead of time. A possible, however less suitable, alternative is to let the control unit 28 control the pump 23. In such an embodiment there is no direct need for the valve 22, but the pump 23 can be connected directly to the conduit 13 and the conduit 14 directly to the column 24. An obvious drawback of such an arrangement is that it is not possible to perform elution immediately following the sample application through the same system, but a separate elution system has to be used. The doses will also be less reliable because of unavoidable flow variations when switching the pump 23 on and off. When using the system for gradient elution, i.e. when the driving solution and the sample solution are to be applied to the column in proportions varying with time, it is preferred to use a more sophisticated control unit 28 which permits continous or a stepwise change of the time relation between the elution position and the sample application position (which in this case also is an elution position). In order obtain optimal results it is for this use suitable to provide a mixing chamber between the valve 22 and the column 24.

As mentioned above it is as an alternative possible to charge exactly the desired amount of sample ("one-shot dose") in the sample solution chamber 6. In this case there is no need to exactly control of the valve 22 since, as has been explained above, the sample solution chamber 6 in this case will be completely emptied and immediately followed by driving solution from the driving solution chamber 5 thanks to the bypass slots 21 in the container tube 1 (see FIGS. 1 and 2).

The invention is, of course, not limited to the embodiments specifically described above and shown in the drawings as concerns detail design and field of use, but many modifications and variations are possible within the scope of the subsequent claims.

What I claim is:

1. An arrangement for applying a sample solution on a liquid chromatographic column, comprising
    (a) a sample container having uniform cross section,
    (b) a piston adapted to move along the axis of said container, sealingly contacting the side walls of the container and dividing the container into a driving solution chamber and a sample solution chamber,
    (c) a first passageway for the introduction and removal of driving solution to and from said driving solution chamber,
    (d) a second passageway for the introduction and removal of sample solution to and from said sample solution chamber,
    (e) pumping means for pumping a driving solution into said driving solution chamber through said first passageway,
    (f) a sample solution reservoir and conduits connecting said reservoir to said second passageway,
    (g) at least one driving solution reservoir and conduits connecting said reservoir to said first passageway,
    (h) a chromatographic column, and
    (i) a valve means (A) interconnecting said sample solution reservoir and said sample solution chamber and (B) interconnecting said driving solution reservoir with said driving solution chamber and (C) interconnecting said pumping means to said driving solution chamber and (D) interconnecting said pumping means with said chromatographic column so that
        (1) when driving solution is pumped into the driving solution chamber it will displace the piston so as to decrease the volume of the sample solution chamber and discharge from the sample solution chamber an amount of sample solution to the chromatographic column which is directly proportional to the amount of driving solution pumped into said driving solution chamber, and
        (2) when sample solution is pumped from the sample solution reservoir into the sample solution chamber it will move the piston so as to decrease the volume of the driving solution chamber.

2. An arrangement according to claim 1 including means for connecting the driving solution chamber with the outlet from the sample solution chamber after all sample solution has been discharged from the sample solution chamber.

3. An arrangement according to claim 2 wherein said connection means comprise at least one recess provided in the inner wall of the container at the bottom end of the sample solution chamber.

4. An arrangement according to claim 1 wherein the piston is connected to a piston rod, which can be controlled from the exterior of the container to permit manual displacement of the piston in the container.

5. A method of supplying a sample solution to a liquid chromatographic column by utilizing a driving solution stream as the driving source, comprising the steps of pumping the driving solution into a variable volume driving solution chamber so as to displace a freely movable piston so that it decreases the volume of a sample solution chamber and thereby forces a sample solution out of the sample solution chamber and into said chromatographic column, said displacement of said piston being carried out in a manner such that the amount of the discharged sample solution is directly proportional to the amount of the driving solution pumped into the driving solution chamber, said piston preventing mixing of the driving solution with the sample solution in the sample solution chamber.

6. A method according to claim 5 further comprising the steps of interrupting the supply of the driving solution to the driving solution chamber when the desired amount of sample solution has been discharged into said column, and thereafter supplying driving solution directly to the column.

7. A method according to claim 6 wherein the driving solution is supplied to the driving solution chamber and the sample solution is supplied to the column via a valve device which is adjustable between a sample application position and an elution position.

8. A method according to claim 7 comprising the step of setting the valve device in said sample application position for a time corresponding to the feeding of a desired amount of sample solution, and then resetting the valve device to said elution position.

* * * * *